United States Patent [19]

Enjoji

[11] 4,408,611
[45] Oct. 11, 1983

[54] PROBE FOR ULTRASONIC IMAGING APPARATUS

[75] Inventor: Susumu Enjoji, Ootawara, Japan

[73] Assignee: Tokyo Shibaura Denki Kabushiki Kaisha, Kawasakishi, Japan

[21] Appl. No.: 238,203

[22] Filed: Feb. 26, 1981

[30] Foreign Application Priority Data

Jul. 3, 1980 [JP] Japan .................................. 55-89990

[51] Int. Cl.³ ............................................. A61B 10/00
[52] U.S. Cl. ................................... 128/660; 604/116
[58] Field of Search ......................... 128/660, 663, 348

[56] References Cited

U.S. PATENT DOCUMENTS

| 4,029,084 | 6/1977 | Soldner ........................ | 128/660 |
| 4,108,165 | 8/1978 | Kopp et al. .................. | 128/660 |
| 4,289,139 | 9/1981 | Enjoji et al. ................. | 128/660 |

OTHER PUBLICATIONS

Ultrasonic Aspiration Biopsy Techniques, Drs. Barry B. Goldberg & Howard M. Pollack, J. of Clinical Ultrasound, vol. 4, No. 2, Apr. 1976, pp. 141-151.

*Primary Examiner*—Kyle L. Howell
*Assistant Examiner*—Mitchell Shein
*Attorney, Agent, or Firm*—Finnegan, Henderson, Farabow, Garrett & Dunner

[57] ABSTRACT

An ultrasonic probe for receiving therethrough a puncturing cannula, the probe comprising a support member having at least one substantially planar surface and including a plurality of ultrasonic transducer elements arranged in at least one row of the one planar surface, a pyramid-shaped space formed in the member, the space having a V-shaped cross section, the apex of the V comprising a first slot between converging walls of the space and lying substantially at the center of the row of transducer elements, the space opening through a wall of the support member substantially perpendicular to the one planar surface; and an auxiliary member substantially complementary in shape to the space and having a pair of tapering walls conforming to the converging walls, the inner edges of the tapering walls forming a second slot lying substantially in the plane of the planar surface and overlying the edges of the converging walls forming the first slot, the side edges of the tapering walls conforming on one side to the opening of the space in the perpendicular wall and terminating on the other side in a back wall perpendicular to the tapering walls, the auxiliary member including a pair of opposing partitions parallel to the back wall and spaced therefrom a predetermined distance, and the faces of the opposing partitions forming a uniform gap of substantially the width of said predetermined distance, said gap opening into said second slot and said predetermined distance being greater than the diameter of the cannula.

1 Claim, 5 Drawing Figures

PROBE FOR ULTRASONIC IMAGING APPARATUS

BACKGROUND OF THE INVENTION

This invention relates to a probe for ultrasonic imaging apparatus and, more particularly, to such apparatus used in the diagnosis of a portion of a living human body pierced by a cannula, as in a biopsy.

A biopsy is a necessary examination for diagnosis of various diseases, especially a blood disease. Presently, the biopsy has ordinarily been performed to withdraw tissues or body fluids by a suitable puncturing cannula from the organs of a human body, such as a liver or kidneys, according to the objectives of the diagnosis. Additionally, in a method for imaging a blood vessel utilizing X-ray photography, for example, a blood vessel or the like is pierced by a cannula and a contrast medium is injected into the blood vessel through the cannula by an injector for discovering morbid changes in the cerebrum, heart, abdominal organs or limbs by X-ray photography.

In other examples, amniotic fluid is withdrawn from the uterus through a cannula, or a medication or blood is injected into the fetal body for diagnosis of a pregnant woman.

In the above-mentioned cases, it is necessary that rigid precaution be made that the puncturing cannula does not damage tissue unnecessarily, that tissue is not misguidedly withdrawn from undesired body areas, and that the contrast medium is not misguidedly injected into the wrong portion of the subject.

In the past, the surgeon performing the operation of puncturing the human body with a cannula has, for the most part, had to relay on his own knowledge, experience and intuition. Recently, however, it has become known to utilize ultrasonic imaging to display tomographic images of the subject, as the body is being pierced by the cannula. For effectively using such ultrasonic imaging apparatus, while the cannula is piercing the subject, it is necessary to accurately display the internal objective in the tomographic image by means of the ultrasonic echo image of the puncturing cannula at the time of the piercing. Moreover, it is necessary that sufficient detail be displayed so that the surgeon can make a proper choice of the course of the cannula into the internal diagnosis portion of the objective as displayed. An ultrasonic probe satisfying these two main conditions is already known, as described, for example in U.S. Pat. No. 4,029,084.

In FIG. 1 of this application, there is shown a plurality of ultrasonic transducer elements 3 arranged in a row on the application surface 1 of a support member 2 of such a conventional ultrasonic probe. The elements 3 are individually connected to a cable 4. A guide slot 5 for a puncturing cannula is provided in the support member 2. As shown, the support member 2 is a rectangular block with transducer elements 3 aligned on one face of the block. The guide slot 5 may be formed, for example, through the block and perpendicular to the application face containing the transducer elements. The guide slot 5 preferably tapers from a relatively narrow opening 5a centered among the transducer elements 3 to a relatively wide opening 5b in the face of the block opposite the transducer elements. The surgeon, therefore, inserts the cannula through the slot 5 from the wide opening to the narrow opening, and the cannula can be rotated and shifted obliquely in the tapered slot.

Due to the central position of the cannula among the transducer elements, the cannula can be simultaneously observed by watching the ultrasonic tomographic image of the objective which is obtained with a sequential actuation of the transducer elements 3 at the time the body is pierced by the cannula.

However, sterilization of this conventional ultrasonic diagnosis device presents continuing problems. Although the cannula is completely disinfected before use, it is necessary to sterilize the support member 2 of the ultrasonic probe also because the cannula may be contacted by the guide slot 5 of the support member 2. A gas disinfection method is generally used for sterilization for quick and efficient contact of all surfaces of the support member 2. It has been found that the binding force of the binding agent used to secure the transducer elements 3, and other members not shown, to the support member is weakened, causing their peeling off, because the gas permeates through very small spaces between the joining portions of the support member 2 or between the support member 2 and the plurality of transducer elements. Since the ultrasonic probe must be sterilized repeatedly, not only is the useful life of the probe shortened, but there is the continuing danger that the probe may be rendered useless at very inconvenient times.

Furthermore, the probe often needs to be used on several subjects in quick succession and the sterilization of the probe is inconvenient and time-consuming. Perhaps most importantly, due to its construction, it is not possible to be sure that the probe has been completely disinfected by the gas treatment.

SUMMARY OF THE INVENTION

It is accordingly the object of this invention to provide an ultrasonic probe for use with a puncturing cannula, wherein the possibly infected portions of the ultrasonic probe can be easily and quickly sterilized as required, and the probe is not damaged by the sterilization process, thus lengthening the life of the probe.

Briefly, these and other objects are achieved in accordance with a first aspect of the invention, by constructing an ultrasonic probe for receiving therethrough a puncturing cannula, the probe comprising a support member and an auxiliary member. The support member has at least one planar surface with a plurality of ultrasonic transducer elements arranged in at least one row on the planar surface and a pyramid-shaped space formed in the member. The space has a V-shaped cross section, the apex of the V comprising a first slot between the converging walls of the space and lying substantially at the center of the row of transducer elements. The wide end of the V-shaped space opens through the wall of the support member opposite the planar surface containing the transducer elements. One side of the space opens through a wall of the support member substantially perpendicular to the one planar surface. The inner side of the space is closed by a planar surface of the support member. Preferably, the support member includes a pair of opposed grooves in the surfaces of the converging walls parallel to the perpendicular wall and the closed inner side of the space.

The auxiliary member is complementary in shape to the pyramid-shaped space and has a pair of tapering walls conforming to the converging walls. The inner edges of the tapering walls form a second slot lying substantially in the plane of the one planar surface and overlying the edges of the converging walls forming the first slot. The side edges of the tapering walls conform on one side to the opening of the space in the perpendicular wall of the support member and terminate on the other side in a back wall perpendicular to the tapering walls.

The auxiliary member includes a pair of opposing partitions parallel with the back wall and spaced therefrom a predetermined distance, the faces of the opposing partitions forming a uniform gap opening at its lower end into the second slot. The gap has substantially the width of the predetermined distance which is greater than the diameter of the cannula to be utilized.

Preferably, the tapering walls of the auxiliary member include a pair of projections on their outer surfaces conforming with and fitting into the pair of grooves when the auxiliary member is installed in the support member.

Preferably, also at least the auxiliary member is formed of elastic, transparent synthetic resins and said tapering walls include tabs on their free edges for compressing the elastic tapering walls toward each other for installation of the auxiliary member into the support member.

DESCRIPTION OF THE PREFERRED EMBODIMENT

I will now describe the preferred embodiment of this invention by reference to the drawings.

Figure 1:
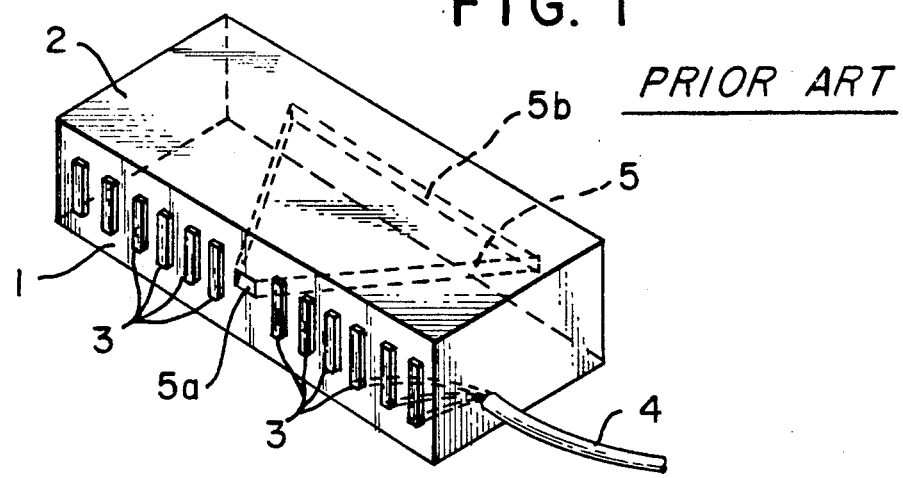
FIG. 1 is a schematic perspective view to illustrate the construction of a prior art ultrasonic probe having a guide slot for a puncturing cannula.
Figure 2:
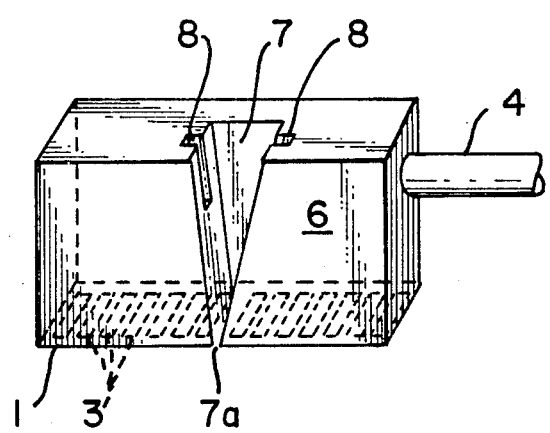
FIG. 2 is a schematic perspective view to illustrate the construction of a support member of an ultrasonic probe according to an embodiment of this invention.

In FIG. 2 in which portions of the construction similar to ones in FIG. 1 are marked with same reference numerals, a plurality of ultrasonic transducer elements 3 are arranged in at least one row on the application surface 1 of a rectangular block-shaped support member 6 of an ultrasonic probe. Signals for actuating the transducer elements and ultrasonic echo signals received by the transducer elements are transmitted to a transmitting-receiving part (not shown) of an ultrasonic diagnosis apparatus through a connection cable 4 connected to each transducer element.

The support member 6 is provided with an inverted pyramid-shaped space 7 which opens at its apex in a slot 7a centered in the row of transducer elements 3 and at its base in the plane of the face of the block-shaped support member 6 opposite the transducer elements. A cross section of the space 7 is substantially in the form of an isosceles triangle. One triangular side of the space 7 opens into a side of the support member 6 perpendicular to the application face 1 bearing the ultrasonic transducer elements 3. Furthermore, a pair of grooves 8 having a defined depth is cut into the two converging surfaces which meet in the slot 7a and incline away from the application surface 1 of the support member 6. The outer ends of the grooves 8 are open and in the plane of the base of the pyramid-shaped space 7.

Figure 3:
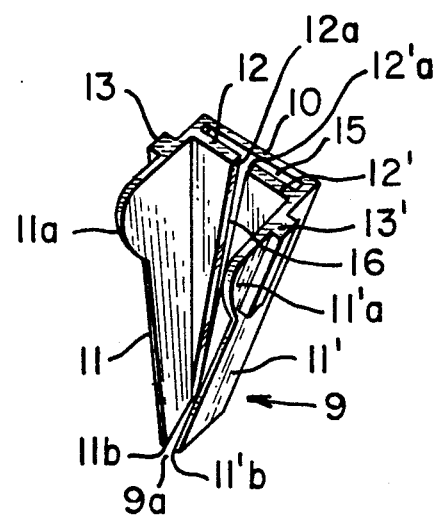
FIG. 3 is a schematic perspective view to illustrate the construction of an auxiliary member for being removably installed in the support member shown in FIG. 2.

FIG. 3 shows a wedge-shaped auxiliary member 9 for guiding the puncturing cannula into the subject. The auxiliary member 9 may be made from elastic synthetic resins, for example, acrylic resins, and fits into the pyramid-shaped space 7 of the support member 6 of the ultrasonic probe. The auxiliary member 9 for guiding the cannula is substantially complementary in shape to the pyramid-shaped space 7 in the support member 6 and has projections 13, 13' on the outer surface of its walls, 11, 11' for fitting into the grooves 8. The walls 11, 11' taper toward each other conforming to the shape of the space 7 and terminate in a slot 9a. The edges 11b, 11'b of the walls 11, 11', forming the slot 9a are substantially planar with the surface 1 of the support member 6, upon insertion of the auxiliary member 9 into the space 7. By this configuration, a cannula inserted through the slot 9a does not contact the support member 6.

A pair of partitions 12, 12' extend toward each other, respectively, from the inner surfaces of the walls 11, 11' and parallel to the wall 10 of the auxiliary member 9 which is complementary in shape to the other triangular end of the space 7. The partitions 12, 12' are spaced from the wall 10 by a distance to permit a cannula to be moved obliquely in the slot 15 formed by the partitions 12, 12' and the wall 10. The opposed surfaces 12a, 12'a of the partitions 12, 12' are separated by a gap 16 of sufficient width to permit a cannula to be inserted lengthwise through the gap. Customarily, a cannula used in the surgical procedure in question is about 2 mm in diameter. Therefore, the widths of the slot 15 and the gap 16 are preferably slightly more than 2 mm.

Figure 4:
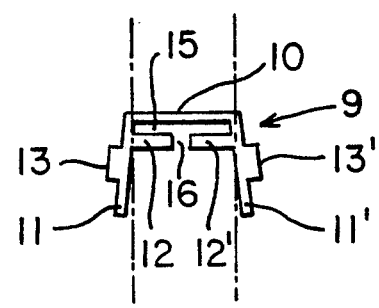
FIG. 4 is a plan view of the auxiliary member shown in FIG. 3.

Substantially semicircular projections 11a, 11'a are respectively defined at the free side edges of the side walls 11, 11' of the auxiliary member 9 so that an operator can easily elastically deform the elastic walls 11, 11' with his hand. FIG. 4 shows a plan view of the auxiliary member in its free state. The elastic walls 11, 11' are formed at slightly obtuse angles with the wall 10 so that, when installed in the support member 6, the walls 11, 11' are under tension.

Although such an auxiliary member 9, as described above, is generally produced by a diecasting, it may be produced by other manufacturing methods known in the art.

In operation, the auxiliary member 9 can be quickly, easily and completely sterilized without involving the support member 6 with its transducer elements 3. Since the cannula comes in contact only with the auxiliary member, the support member does not have to be sterilized before each use. The auxiliary member 9 may be sterilized by any convenient means.

Since walls 11, 11' of the auxiliary member 9 always face outwardly from each other in the free state, they can be deformed inwardly by grasping the semicircular projections 11a, 11'a defined on the outer edges of the side walls 11, 11' with the operator's fingers and the auxiliary member inserted into the pyramid-shaped space 7. When the auxiliary member 9 is smoothly fitted into the support member 6 and the projection 13, 13' defined on the side walls 11, 11' of the auxiliary member 9 are fitted into the grooves 8, the auxiliary member 9 is securely fitted in the space 7 with the internal stress of the side walls 11, 11' retaining the auxiliary member 9 in position.

Figure 5:
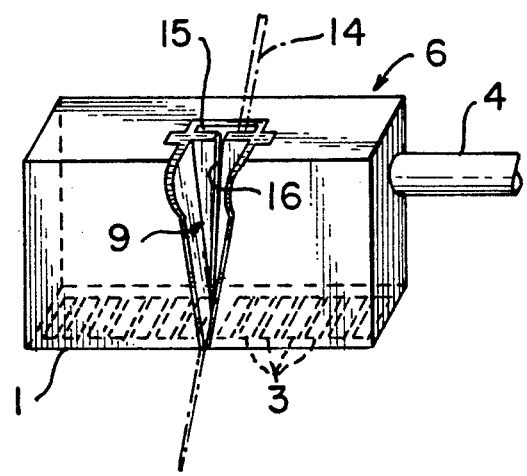
FIG. 5 is a schematic perspective view to illustrate the ultrasonic probe of the invention for use with a puncturing cannula, the auxiliary member shown in FIG. 3 being installed in the support member shown in FIG. 2.

Shown in FIG. 5 is the state of the probe after installing the auxiliary member 9 into the support member 6 with the cannula 14 defined in shadow lines. Since the guide slot 15 tapers inwardly, the cannula is guided by the surgeon into the portion of the slot 9a within the slot 7a. The gap 16 permits the cannula 14 to be moved into and out of the slot 15 horizontally by the surgeon with a minimum of delay.

Furthermore, the lower end of the guide slot 15 is positioned substantially at the center of the row of transducer elements 3 arranged on the application surface 1 of the support member 6 and its maximum upper end is extended in the direction of the row of transducer elements. Consequently, the puncturing cannular can be operated in the guide slot 15 at an arbitrary angle by movement in the guide slot 15 without getting out of the scan region of the ultrasonic beams aimed at the objective as transmitted from the row of transducer elements.

An advantage of the structure of the invention is that the ultrasonic probe can be removed from the surface of the subject's body during the operation while leaving the cannula in place. This can be very advantageous in X-ray photography wherein a contrast medium is being injected by the cannula, after proper location by the tomography. Due to the gap 16 and the slots 9a and 7a the support member 6 can be moved away from the cannula 14 in a direction perpendicular to the direction of the row of transducer elements 3, thus leaving the cannula in place for continuing the injection.

Since the auxiliary member 9 may be formed of plastic and manufactured inexpensively, it is expendable and may be thrown away after use. On the other hand, if desired, the auxiliary member may be efficiently reused. It is easily sterilized and the auxiliary member 9 is the only portion of the ultrasonic probe coming in contact with the cannula.

Furthermore, the support member itself of the ultrasonic probe can be easily and less expensively manufactured because the support member having the pyramid-shaped space 7 can be produced by diecasting.

What is claimed is:

1. An ultrasonic probe for receiving therethrough a puncturing cannula, said probe comprising:

a support member having at least one substantially planar surface, said member including a plurality of ultrasonic transducer elements arranged in at least one row on said one planar surface, a pyramid-shaped space formed in said member, said space having a V-shaped cross section, the apex of the V comprising a first slot between converging walls of the space and lying substantially at the center of said row of transducer elements, said space opening through a wall of the support member substantially perpendicular to said one planar surface; and a wedge-shaped auxiliary member removably inserted into said space, said auxiliary member being substantially complementary in shape to said space and having a pair of tapering walls conforming to said converging walls, the inner apex edges of said tapering walls forming a second slot lying substantially in the plane of said planar surface and overlying the edges of the converging walls forming the first slot, the side edges of said tapering walls being free and conforming on one side to said opening of said space in said perpendicular wall and terminating on the other side in a back wall perpendicular to said tapering walls, said auxiliary member including a pair of opposing partitions extending from said tapering walls parallel to said back wall and spaced therefrom a predetermined distance, and the surfaces of said opposing partitions facing away from said tapering walls forming a uniform gap of substantially the same width as said predetermined distance, said gap opening into said second slot and said predetermined distance being slightly greater than the diameter of said cannula, the portions of said tapering walls being unobstructed between said partitions and said edges on one side for forming said free edges of said auxiliary member, and wherein said probe also includes a pair of grooves in the inner surfaces of said converging walls parallel to said perpendicular wall, and a pair of projections on the outer surfaces of said tapering walls, said projections conforming with and fitting into said grooves when said auxiliary member is installed in said support member and being positioned on the outer surfaces of said unobstructed portions of said tapering walls, and said tapering walls are formed of elastic synthetic resin and include projecting tab means on said free edges, said unobstructed portions of said elastic tapering walls being manually compressible toward each other for installation of said auxiliary member substantially horizontally into said support member, said installation including the insertion of said projections into said grooves.

* * * * *